United States Patent [19]
Pope

[11] Patent Number: 5,803,074
[45] Date of Patent: Sep. 8, 1998

[54] VALVE FOR RESUSCITATOR APPARATUS

[75] Inventor: James W. Pope, North Fort Myers, Fla.

[73] Assignee: Smiths Industries Medical Systems, Inc., Keene, N.H.

[21] Appl. No.: 758,175

[22] Filed: Nov. 25, 1996

[51] Int. Cl.[6] .............................. A62B 7/00; A61M 16/00
[52] U.S. Cl. .............................. 128/205.24; 128/203.11; 128/205.17
[58] Field of Search ................... 128/205.24, 207.12, 128/207.16, 202.28, 202.29, 203.11, 205.16, 205.17, 200.29; 137/855

[56]  References Cited

U.S. PATENT DOCUMENTS

| | | | |
|---|---|---|---|
| 2,119,446 | 5/1938 | Sholes | 128/203 |
| 2,225,201 | 12/1940 | Anderson | 128/188 |
| 2,300,273 | 10/1942 | Connell | 128/203 |
| 3,079,915 | 3/1963 | Stanton | 128/29 |
| 3,473,529 | 10/1969 | Wallace | 128/145.7 |
| 3,952,335 | 4/1976 | Sorce et al. | 128/207.16 |
| 4,179,051 | 12/1979 | Thomas | 222/494 |
| 4,239,038 | 12/1980 | Holmes | 128/205.24 |
| 4,253,491 | 3/1981 | Worthen et al. | 137/599 |
| 4,274,404 | 6/1981 | Molzan et al. | 128/205.24 |
| 4,510,933 | 4/1985 | Wendt et al. | 128/207.14 |
| 4,538,620 | 9/1985 | Nowacki et al. | 128/207.16 |
| 4,696,263 | 9/1987 | Boyesen | 137/855 |
| 5,109,840 | 5/1992 | Daleiden | 128/205.13 |
| 5,217,006 | 6/1993 | McCulloch | 128/205.13 |
| 5,222,491 | 6/1993 | Thomas | 128/205.13 |
| 5,301,667 | 4/1994 | McGrail et al. | 128/205.14 |
| 5,357,946 | 10/1994 | Kee et al. | 128/200.24 |
| 5,357,951 | 10/1994 | Ratner | 128/205.24 |
| 5,404,873 | 4/1995 | Leagre et al. | 128/204.18 |
| 5,427,091 | 6/1995 | Phillips | 128/205.15 |
| 5,655,898 | 8/1997 | Hashimoto et al. | 137/855 |

FOREIGN PATENT DOCUMENTS

| | | | |
|---|---|---|---|
| 0 367 285 | 5/1990 | European Pat. Off. . | |
| 24 24 798 | 11/1975 | Germany | A61M 16/00 |
| 1 374 583 | 11/1974 | United Kingdom | A61M 16/00 |
| 1 498 059 | 1/1978 | United Kingdom | A61M 16/00 |
| 2 145 335 | 3/1985 | United Kingdom | A61M 16/00 |

OTHER PUBLICATIONS

International Search Report on Application No. PCT/US97/21162, dated Mar. 25, 1998.

*Primary Examiner*—John G. Weiss
*Assistant Examiner*—V. Srivastava
*Attorney, Agent, or Firm*—Marshall, O'Toole, Gerstein, Murray & Borun

[57]  ABSTRACT

This disclosure relates to a valve for a resuscitator apparatus including a resuscitator bag and a reservoir bag. The valve is mounted in a coupling between the two bags. The valve comprises a reed flapper in a housing, the reed flapper having one side exposed to the interior pressure and another side exposed to the ambient pressure. The reed flapper is movable in response to a higher interior or ambient pressure (a pressure differential), to open a housing port to allow flow out of or in to the reservoir bag interior. The valve further includes a biasing part to increase the opening pressure differential in one direction or the other.

18 Claims, 7 Drawing Sheets

FIG. 15

VALVE FOR RESUSCITATOR APPARATUS

FIELD AND BACKGROUND OF THE INVENTION

This invention relates to respiratory care apparatus, and more particularly to a valve for use in a disposable manual resuscitator.

Manual resuscitators are well known and various designs are described in numerous patents such as the W. Cook U.S. Pat. No. 4,774,941. The Cook resuscitator includes a valve assembly including a duckbill-type valve connected between an outlet end of a resuscitator or squeeze bag and, for example, a patent face mask. A gas, such as air and/or a mixture of air and oxygen, for example, enters the squeeze bag through an intake valve at an intake end of the squeeze bag.

In a situation where an auxiliary gas such as oxygen is fed into the resuscitator bag through the intake valve, a bag reservoir may be connected to the resuscitator bag at the intake end. In this type of arrangement, an oxygen supply tube is connected to feed oxygen into the bag reservoir, and the resuscitator bag draws the oxygen from the reservoir bag.

In such a construction, if the quantity of oxygen fed from the supply tube into the bag reservoir exceeds the quantity being inspired by the patient, a positive pressure may build up in the bags, which may be detrimental to the patient. On the other hand, if the quantity being inspired is greater than that supplied by the reservoir bag, there may be an insufficient pressure and supply for the patient.

German Offenlegungsschrift No. 224,798 and U.K. patent No. 1,498,059 show an arrangement of a resuscitator bag and a reservoir bag attached to an intake of the resuscitator bag. Between the two bags is provided a valve arrangement which, according to the patents, is supposed to hold the internal pressure of the bags at substantially atmospheric pressure. While the arrangement shown in these patents may function as purported in the patents, the arrangement appears to be relatively complex and expensive since two valves are required.

It is a general object of the present invention to provide an improved valve for maintaining substantially atmospheric pressure in the reservoir bag.

SUMMARY OF THE INVENTION

A valve constructed in accordance with the present invention is designed for use in a coupling between a reservoir bag and a resuscitator bag, the coupling including a wall separating an interior or enclosed space from the ambient or exterior space. The valve includes a valve body having a first port communicating with the ambient space and a second port communicating with the interior space. The valve further includes a reed flapper attached to said valve body adjacent a selected one of said first and second ports. The flapper has a normal or inactive position where it substantially closes the selected port but is movable to open the selected port due to a pressure difference between the ambient and interior spaces. The flapper is movable to open the selected port in response to a pressure differential between the ambient and interior pressures. The valve preferably further includes biasing means which opens the selected port when the pressure difference in one direction is different from the pressure difference in the other direction.

BRIEF DESCRIPTION OF THE DRAWINGS

The invention will be better understood from the following detailed description taken in conjunction with the accompanying figures of the drawings, wherein.

DETAILED DESCRIPTION OF THE INVENTION

Figure 1:
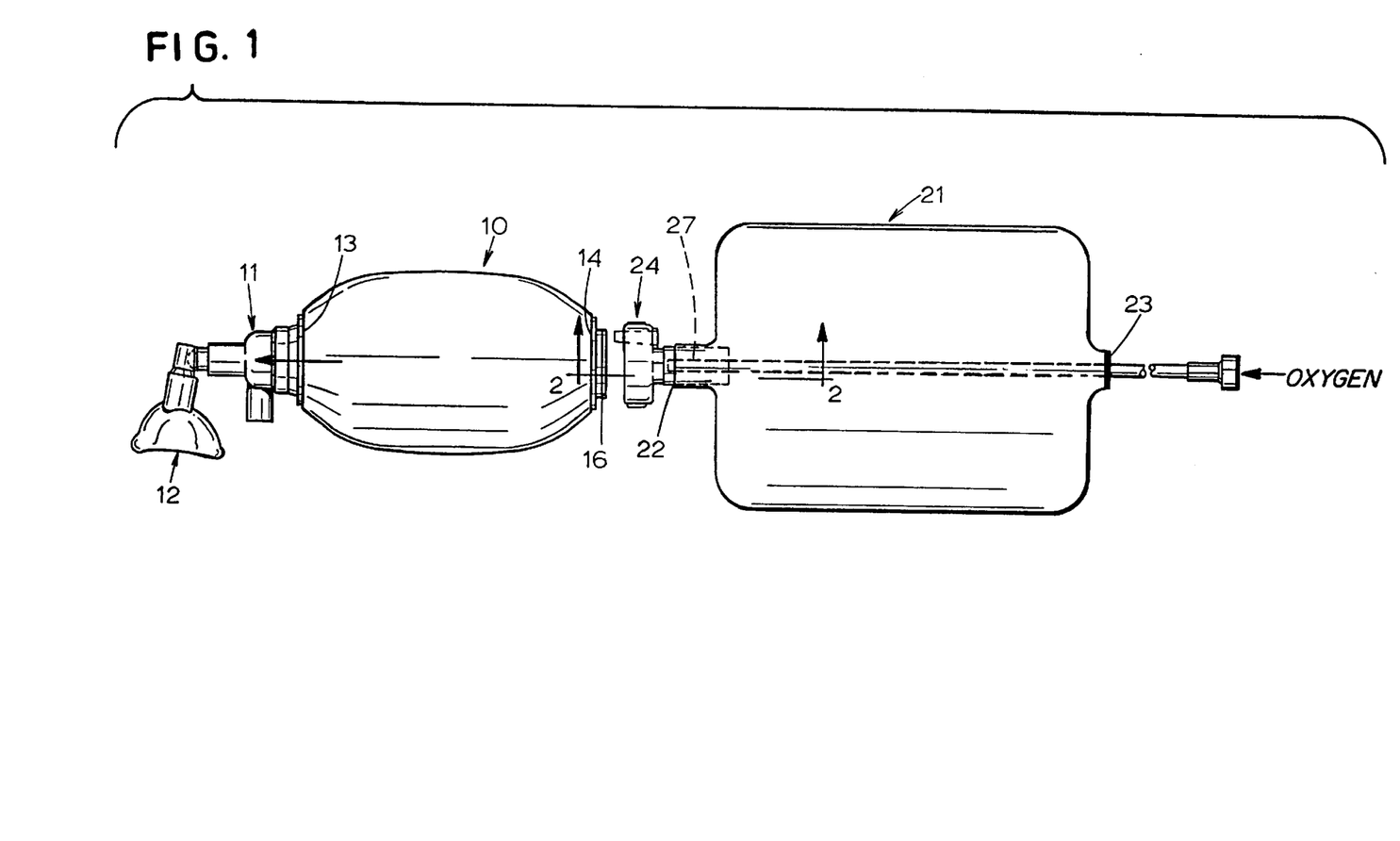
FIG. 1 is a diagrammatic view of resuscitator apparatus including a valve constructed in accordance with the present invention.

FIG. 1 illustrates manual resuscitation apparatus for use with a patient requiring assistance in breathing. The apparatus includes a resuscitator or squeeze bag 10 connected by a valve assembly 11 to a patient face mask 12 or other device for connection with a patient. The valve assembly 11 and the face mask 12 may be of the type described in more detail in the previously mentioned Cook patent and therefore is not described in further detail herein. The bag 10 includes an outlet opening 13 which is connected to the valve assembly 11, and an inlet opening 14, a conventional one-way or check valve assembly 16 being fastened to the inlet opening 14. During operation of the apparatus, a person compresses the bag 10 and this action causes the check valve assembly 16 to close and the gas within the bag 10 to be forced out of the outlet opening 13, through the valve assembly 11 and the mask 12 to the patient. When pressure on the bag 10 is released, it returns to its normal inflated condition (illustrated in FIG. 1) during which time the valve assembly 11 closes and additional gas is drawn into the bag 10 through the inlet valve assembly 14.

The apparatus shown in FIG. 1 further includes a reservoir bag 21 having an outlet opening 22 and an inlet opening 23. The outlet opening 22 is connected by a coupling 24 to the check valve assembly 16, the coupling 24 being better illustrated in FIGS. 2 through 4. In the embodiment of the invention illustrated in FIGS. 1 through 4, a gas supply tube 26 extends through the inlet opening 23, and the opening 23 is sealed around the outer periphery of the tube 26. The tube 26 is adapted to be connected to a supply of an auxiliary gas such as oxygen. The tube 26 extends through the interior of the reservoir bag 21 and its outlet end portion 27 is fastened to the coupling 24.

Figure 2:
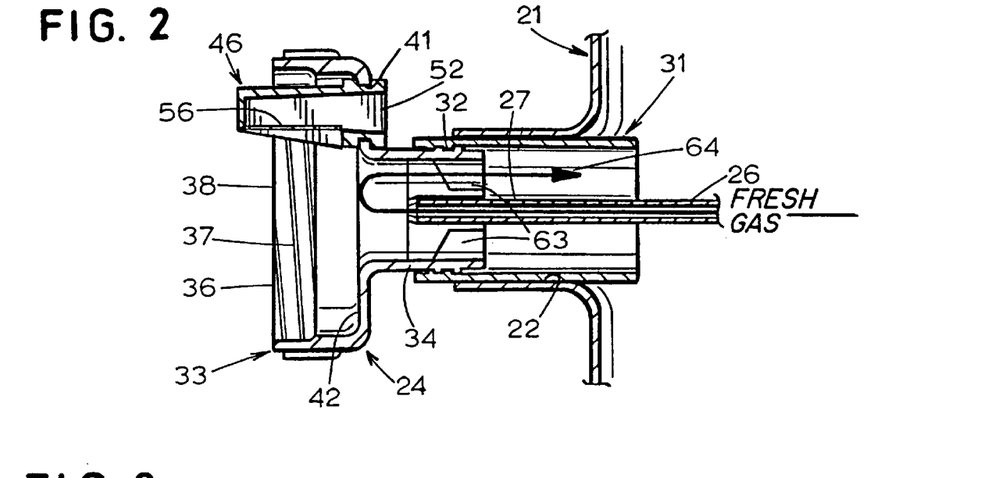
FIG. 2 is a sectional view taken on the line 2—2 of FIG. 1 and showing the valve.

With specific reference to FIG. 2, sealed to the outlet opening 22 of the reservoir bag 21 is a tubular adaptor 31 which is fastened to the coupling 24 by a threaded connection, for example, indicated by the reference numeral 32. The coupling 24 includes a tubular housing 33 that includes an intake portion 34 which is attached at 32 to the adaptor 31, and a radially enlarged portion 36 which is fastened to the check valve assembly 16 shown in FIG. 1. In the present instance, the enlarged portion 36 includes internal threads 37 designed to screw onto threads formed on the exterior of the valve assembly 16. The enlarged portion 36 cooperates with the valve assembly 16 to form an interior enclosed space indicated by the reference numeral 38 in FIG. 2, which is in flow communication with the interior of the adaptor 31 and with the interior of the reservoir bag 21. The interior space 38 is also in flow communication, through the one-way check valve assembly 16, with the interior of the resuscitator bag 10.

The coupling housing 33 is formed by a wall 42; an opening 41 is formed in the wall 42 and a valve 46 is secured within the opening 41.

The valve 46 is best illustrated in FIGS. 5 through 10, and includes a main body 47. A groove 48 is provided in the outer periphery at one end of the main body 47, the groove 48 receiving the edge portion of the opening 41 for securing the main body 47 to the housing 33 and forming a sealed connection between the outer periphery of the body 47 and the housing 33. The main body 57 includes five walls 49 forming a hollow interior 51. First and second ports 52 and 53 are formed in the main body 47, the two ports 52 and 53 connecting the body interior 51 with the exterior or ambient space of the main body. As shown in FIGS. 1 and 2, for example, the valve is mounted in the coupling 24 such that the port 52 is in direct communication with the ambient space at the exterior of the coupling 24 and the reservoir bag 21. The other port 22 faces the interior space 38 of the coupling 24, as shown in FIG. 2.

Figure 10:
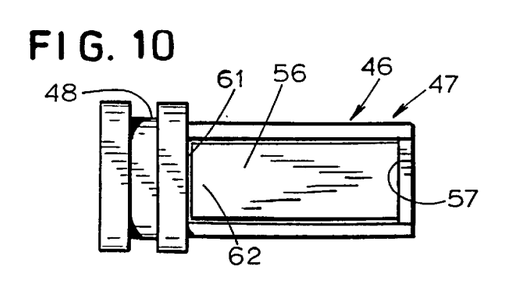

A valve reed or flapper 56 extends across the second port 53, and in its inactive or closed position (illustrated in FIGS. 2 and 6), the flapper 56 extends across the port 53 and substantially closes the port. The flapper 56, in this embodiment of the invention, is formed integrally (as by molding a plastic body and flapper) with the main body 47 and is hinged, as indicated by the numeral 57, at one side of the port 53. From the hinge connection 57, the flapper 56 extends across the port 53 as illustrated in FIGS. 6 and 10, for example. The flapper is flexible, however, and is capable of being flexed either upwardly or downwardly as shown FIGS. 3 and 4 and as indicated by the two arrows 58 in FIG. 6.

From FIG. 6 it will also be noted that the side 61 of the port 53, which is adjacent the outer or free end 62 of the flapper 66, is elongated. The outer end 62 of the flapper 56 is normally (when in its inactive position) adjacent the interior edge 61A of the side 61, the edge 61A being adjacent the interior 51. The flapper 56 does not completely clear the side 61 until it is moved past the other edge 61B of the side 61, the edge 61B being adjacent the interior space 38 of the coupling 24.

Figure 3:
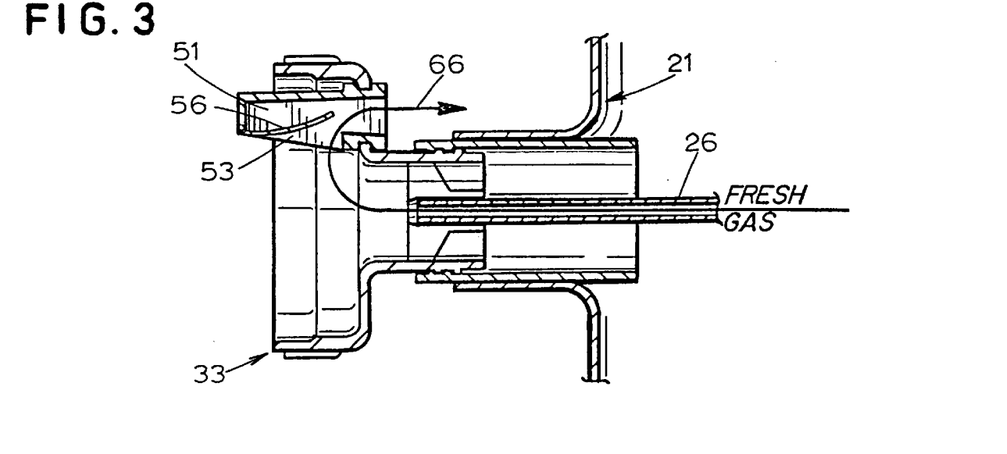
FIG. 3 is a view similar to FIG. 2 but showing another operating position of the valve.
Figure 4:
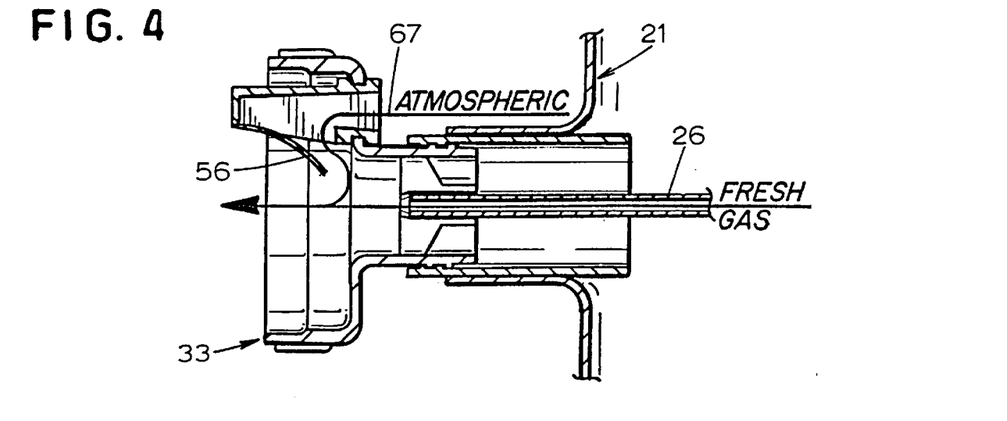
FIG. 4 is another view similar to FIGS. 2 and 3 and showing still another operating position of the valve.
Figures 5, 6:
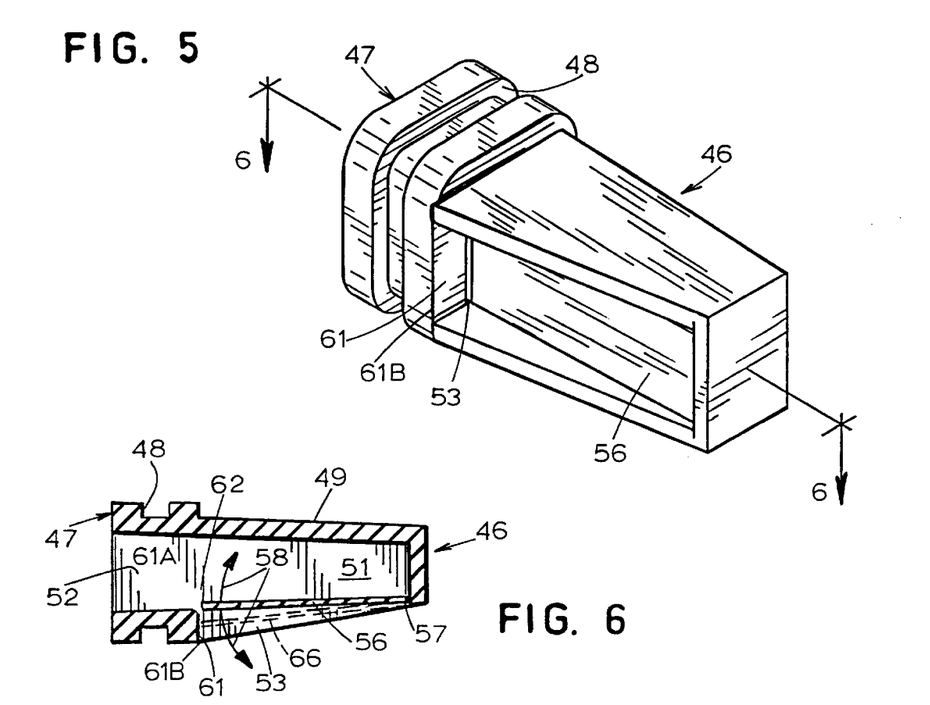
FIG. 5 is an enlarged perspective view of the valve.
FIG. 6 is a sectional view taken on the line 6—6 of FIG. 5.
Figure 7:
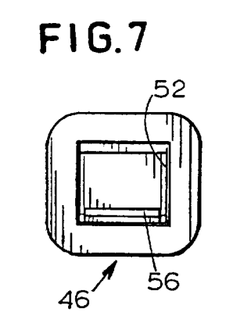
FIGS. 7, 8, 9 and 10 are elevational views showing different sides of the valve shown in FIG. 5.
Figure 8:
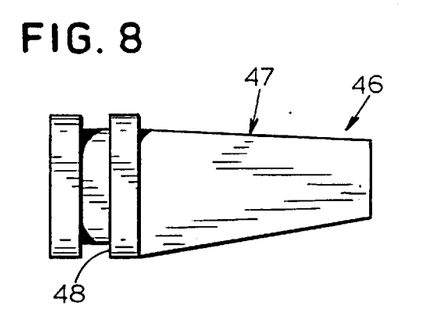
Figure 9:
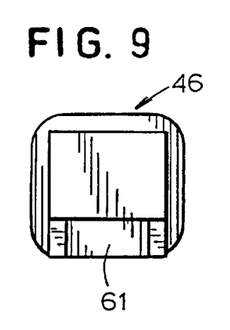

With reference to FIGS. 2, 3 and 4, when the resuscitator apparatus is in use, the tube 26 is connected to a supply of auxiliary gas such as oxygen as previously explained, and the outlet end portion 27 of the tube 26 is held in place between ribs 63 formed on the interior of the portion 34 of the coupling housing 33. Assuming that the resuscitator bag 10 is being collapsed in order to force gas from the interior of the bag 10 through the mask 12 and to a patient (not illustrated), the check valve assembly 16 is closed and the gas flowing through the tube 26 moves in the direction of the arrow 64 shown in FIG. 2 and into the interior of the reservoir bag 21. Normally the flow of the fresh gas is continuous and it is sufficient to fill the reservoir bag 21 to the point where an adequate supply is available when the pressure on the bag 10 is released and it is allowed to expand, at which time fresh gas is drawn into the bag 10 from the reservoir bag 21. However, if the amount of fresh gas flowing in the direction of the arrow 64 is excessive and there is an excess inflow of the gas causing an increased bag 21 pressure above ambient pressure, the higher than ambient pressure within the bag 21 and within the interior space 38 of the coupling 24 exerts pressure on the flapper 56. This interior pressure (see FIG. 3) causes the flapper 56 to bend toward the interior space 51 of the main body 46, whereby the second port 53 is open and allows the excess gas to flow in the direction of the arrow 66 through the opening 63 and 52 to the ambient atmosphere, thereby substantially equalizing the bag 21 pressure with the ambient pressure.

On the other hand, if the amount of fresh gas flowing through the tube 26 is not sufficient to meet the needs of the patient, the expansion of the resuscitator bag 10 results in drawing all of the gas from the reservoir bag 21 and decreasing the pressure within the interior space 38 of the coupling 24, the interior pressure thereby being below the ambient pressure. In this instance, as illustrated in FIG. 4, the flapper 56 bends in the direction of the interior space 38, allowing atmospheric air to flow along the path indicated by the numeral 67 from the atmosphere into the interior space 37, through the valve assembly 16 and into the interior of the resuscitator bag 10.

It will be apparent therefore that the flapper valve 56 is movable when necessary to maintain the pressure of the gas within the reservoir bag 21 substantially at atmospheric pressure, thereby preventing either an excessive pressure or inadequate pressure within the resuscitator bag 10 from harming the patient.

With reference again to FIGS. 4 and 6, as previously mentioned the flapper 56 bends towards the interior space 38 when the ambient pressure is higher than the pressure within the interior space 38. Since the port 53 is substantially closed during the entire time that the end portion 62 is adjacent the elongated side 61, the port 53 will not be completely opened until the end 62 of the flapper 56 is completely clear of the exterior edge 61B of the side 61. As a consequence, the pressure within the interior 51 of the valve body 46 (which is also the ambient pressure) must be slightly higher than the pressure within the interior space 37 (a pressure differential) before ambient air is allowed to flow into the space 38. On the other hand, since the end portion 62 normally is in the neutral or inactive position where it is adjacent the interior edge 61A, only a slight increase in pressure within the space 38 will cause the valve flapper 56 to bend upwardly as shown in 53 and permit the interior gas to flow out into the atmosphere. The dashed line position 66 of the flapper 56 shown in FIG. 6 illustrates an intermediate position of the flapper 56 before the port 53 is fully opened. There is thus a dead zone of movement of the flapper along the edge 61 before the port 53 opens due to a pressure differential, and the elongated side 61 in conjunction with the neutral position of the end portion 62 form a biasing means.

As a consequence, the valve 46 prevents a bag pressure in excess of ambient pressure, but allows a bag pressure slightly below ambient pressure, before opening.

Figure 11:
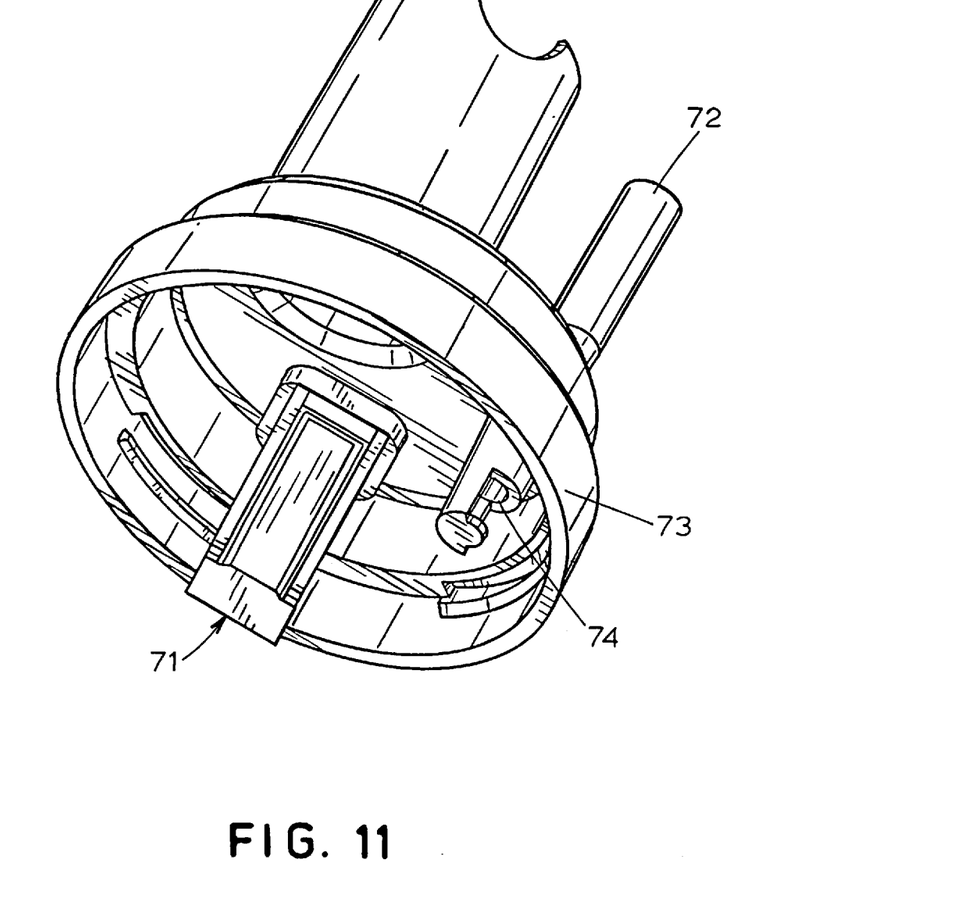
FIG. 11 is a perspective view showing an alternative embodiment of the invention.

In the embodiment of the invention illustrated in FIG. 11, the construction of the valve 71 is identical with that of the valve 46 shown in FIGS. 1 to 10. Whereas in FIGS. 1 through 10 the auxiliary gas supply tube 26 extends through the reservoir bag 21 and terminates within the coupling 24, in the embodiment of the invention shown in FIG. 11, the supply tube 72 is exterior of the reservoir bag and it terminates within the coupling 73. This arrangement permits an opening 74 of the tube 72 to be displaced from the valve 71 and to direct the incoming gas away from the valve 71, so that the flow of the gas will not interfere with the operation of the valve 71.

Figure 12:
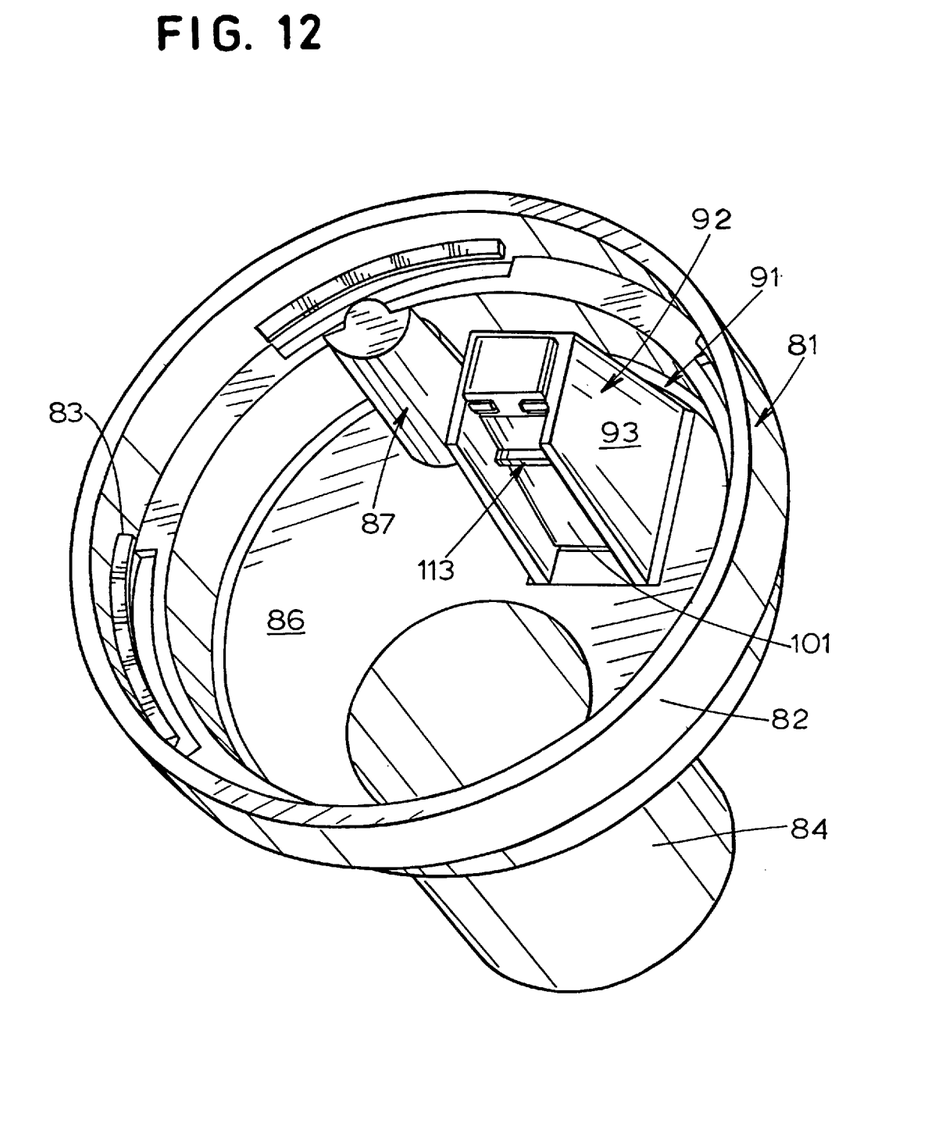
FIG. 12 is a perspective view showing another alternative embodiment of the invention.
Figure 13:
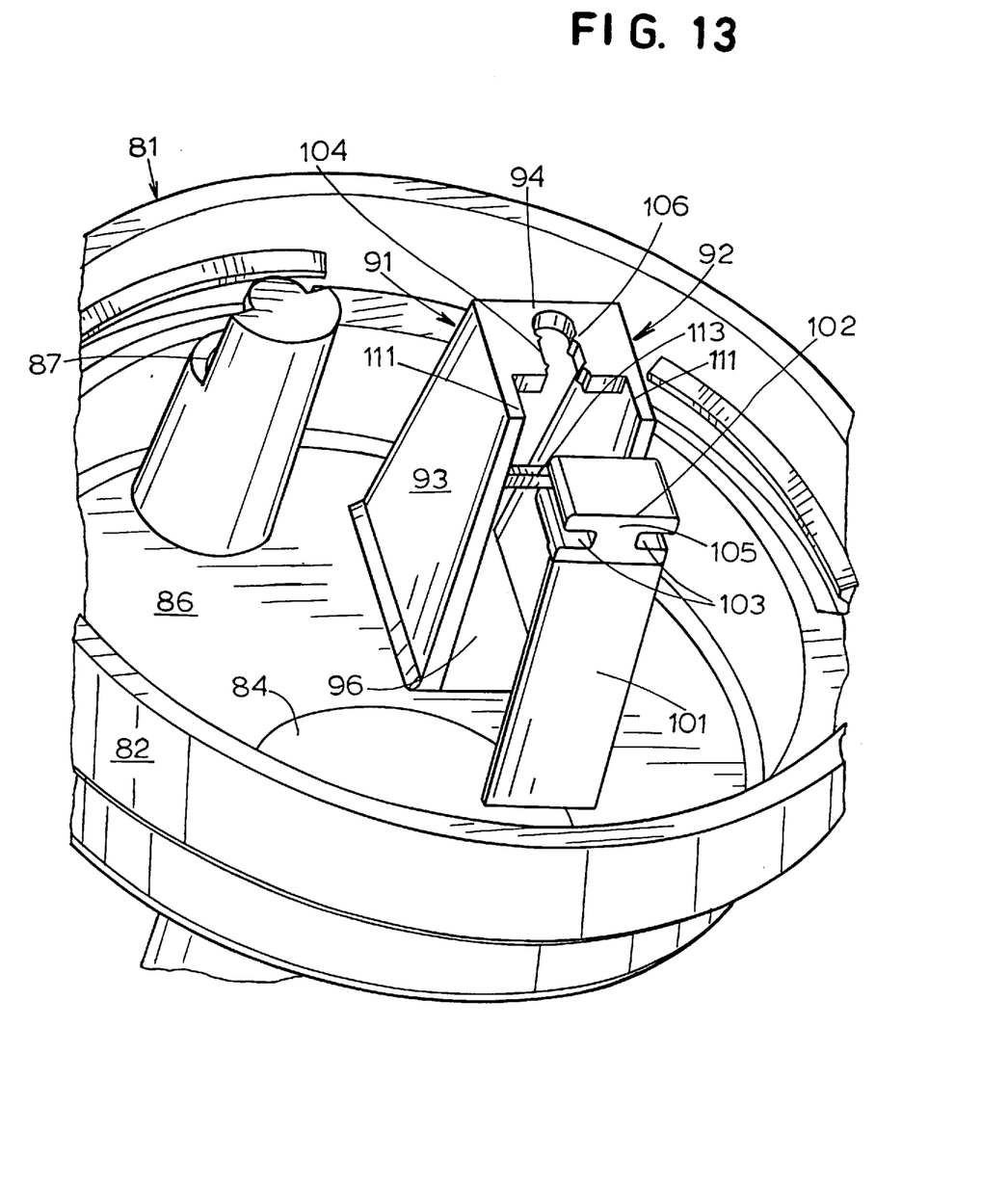
FIG. 13 is an exploded perspective view of the embodiment shown in FIG. 12.
Figure 14:
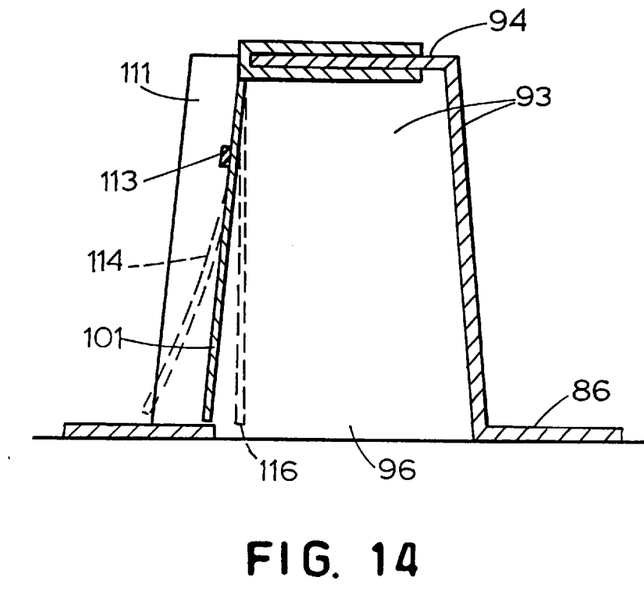
FIG. 14 is a sectional view of a valve of the embodiment shown in FIG. 12.

FIGS. 12 to 14 illustrate another embodiment of the invention, which includes means for providing an additional bias to the valve. A coupling 81 includes a cylindrical wall 82 having internal teeth 83 for attaching the coupling to the bag 10. A tubular part 84 formed on the wall 86 connects the coupling 81 to an adaptor and a reservoir bag. An intake 87 for fresh gas is also formed on the wall 86.

A valve 91 in accordance with this invention is also mounted on the wall 86, and includes a body 92 having three side walls 93 and a top wall 94, the walls 93 and 94, in this specific example, being molded integrally with the coupling wall 86. The walls 93 and 94 form a hollow interior which is located over an opening 96 in the wall 86.

The valve body 92 has an open side that is covered by a reed flapper 101 which is attached to (preferably integrally formed with) a reed base 102. The base 102 includes two parallel slots 103 which extend over and under edge portions of the top wall 94. An opening 104 (FIG. 13) of the top wall 94 receives the center portion 105 of the base 102, and teeth 106 formed along the edge of the opening 104 grip the center portion 105 and hold the two parts in assembled relation.

The two side walls 93 which are adjacent the open side of the body 92 include extended portions 111 which project beyond the normal or neutral position of the reed flapper 101. This arrangement is similar to that illustrated in FIG. 6, and forms means for biasing the valve opening pressure so that a greater pressure differential is required in one direction.

An additional biasing means is provided, which is formed by a crossbeam 113 which extends laterally of the open side of the main body 92. At its ends, the crossbeam is attached to the extended portions 111 of the side walls 93, and it is adjacent one side (in this specific example it is adjacent the outer side) of the reed flapper 101. In this specific example, the crossbeam 113 is about two-thirds of the distance up from the free end of the reed flapper 101, and it is closely adjacent the outer surface of the flapper 101. Consequently, as illustrated by the dashed line 114 position of the flapper 101 (see FIG. 14), the crossbeam increases the internal pressure required to open the valve because only the lower portion (below the crossbeam) is able to flex outwardly. A lower pressure is needed to flex the reed flapper inwardly to the dashed-line position 116 and open the valve for flow in the other direction.

Figure 15:
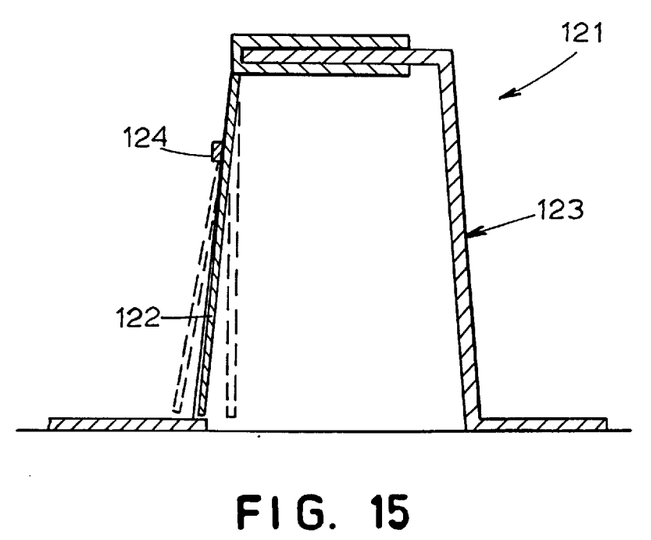
FIG. 15 is a sectional view similar to FIG. 14 but showing still another embodiment of the valve.

FIG. 15 illustrates another alternative embodiment which is similar in construction to the valve 91. The valve 121 includes a reed flapper 122 mounted on a valve body 123 similarly to the valve 91, and a crossbeam 124 is mounted across the outside of the flapper 122, for biasing the valve opening pressure. However, the side walls of the valve body do not have extended portions corresponding to the portions 111 shown in FIGS. 13 and 14.

Consequently, the valve shown in FIG. 5 contains biasing means formed by extended portions of the side walls, the valve shown in FIG. 15 contains biasing means formed by a crossbeam, and the valve shown in FIG. 14 contains two biasing means formed by the extended wall portions and by the crossbeam.

While the crossbeams 113 and 124 are shown on the outside of the reed flappers, they could instead be provided on the interior sides to bias the opening pressure differential in the other direction.

To assemble the reed flapper with the valve body in the embodiments shown in FIGS. 12 to 15, the reed portion is positioned behind the crossbeam and then the reed base is pressed into the opening 104 of the valve body.

As illustrated in FIG. 13, for example, the opening of the fresh gas intake and the reed flapper face away from each other, whereby the flow of the gas does not affect the operation of the valve.

It will be apparent therefore that an improved valve for a resuscitator apparatus has been provided. Only a single valve for both directions of flow is required. The valve may be economically manufactured in one integral piece of molded plastic such as silicone, or it may be manufactured in two molded parts which are easily assembled. The flapper is enclosed within the housing and is not easily tampered with or clogged. Further, bias means is formed by providing an elongated side 61 of the port 53 and by locating the flapper adjacent one edge of the side 61 when in the inactive or normal position of the flapper, and/or by providing a crossbeam. Thus, a dead zone of flapper movement is formed. Instead of the construction illustrated in the drawings, the end 62 of the flapper 56 could have its normal position adjacent the other edge 61B, or its normal position could be intermediate the two edges. A construction is also possible wherein the side 61 is relatively thin (not elongated), and the end 62 of the flapper has its normal position adjacent the thin edge, in which case the port would be opened in either direction by a small difference in pressure.

What is claimed is:

1. A valve for use with resuscitator apparatus including a resuscitator bag, a reservoir bag and a coupling connecting the bags, the coupling including a wall forming an interior space which is in flow communication with the reservoir bag, said valve comprising a valve body having a port formed therein, said valve body being mountable in said wall of said coupling between the interior space and the ambient space, said valve further comprising a reed flapper hinged on said valve body on one side of said port, said reed flapper having a normal position wherein said reed flapper extends across and substantially closes said port, said reed flapper being movable to open said port to enable flow into or out of the interior space.

2. A valve as set forth in claim 1, wherein said reed flapper has first and second opposing sides, each of said sides being exposed to a pressure, and said reed flapper being bendable to open said port in response to a pressure differential between said interior space and said ambient space.

3. A valve as set forth in claim 2, wherein said reed flapper is bendable to enable flow either in a first direction from said interior space toward said ambient space or in a second direction from said ambient space toward said interior space.

4. A valve as set forth in claim 3, wherein said valve further includes biasing means for causing the pressure differential to be greater for flow in one of said directions than in the other of said directions.

5. A valve as set forth in claim 4, wherein said biasing means comprises extended portions of said valve body adjacent said port.

6. A valve as set forth in claim 4, wherein said biasing means comprises a cross beam attached to said body and extending across said port and engageable with said reed flapper.

7. A valve as set forth in claim 1, wherein said reed flapper is molded separately from said valve body and is attached to said valve body.

8. A valve as set forth in claim 1, wherein said reed flapper is formed integrally with said valve body.

9. A valve as set forth in claim 1, wherein said reed flapper and said valve are integrally molded of a plastic.

10. A valve as set forth in claim 4, wherein said greater pressure differential is for flow into said interior space.

11. Resuscitator apparatus, comprising a resuscitator bag, a reservoir bag, a check valve assembly connecting said bags and enabling flow from said reservoir bag into said resuscitator bag, supply means for conducting an auxiliary gas into said reservoir bag, and a valve connected between the interior of said reservoir bag and the ambient space, said valve comprising a reed flapper to enable flow into said reservoir bag interior from said ambient space or out of said reservoir bag to said ambient space.

12. Resuscitator apparatus as set forth in claim 11, and further including a coupling between said bags, said valve being mounted on said coupling.

13. Resuscitator apparatus as set forth in claim 11, wherein said reed flapper is movable in response to a pressure differential between said bag interior and said ambient space.

14. Resuscitator apparatus as set forth in claim 11, wherein said pressure differential is higher in one direction of flow than for the other direction of flow.

15. Resuscitator apparatus as set forth in claim 11, wherein said valve comprises an integrally formed valve body and said reed flapper.

16. Resuscitator apparatus as set forth in claim 15, wherein said valve body has a port formed therein and said reed flapper extends across said port.

17. Resuscitator apparatus as set forth in claim 12, wherein said supply means comprises a tube which extends through said reservoir bag and has an outlet end in said coupling.

18. Resuscitator apparatus as set forth in claim 12, wherein said supply means comprises a tube having an outlet end in said coupling, said outlet end directing the auxiliary gas away from said valve.

* * * * *